United States Patent
Lee et al.

(10) Patent No.: US 9,718,899 B2
(45) Date of Patent: Aug. 1, 2017

(54) ANIONIC POLYMERIZATION INITIATOR HAVING ANIONIC TERMINAL COMPRISING AMINE GROUP, PRODUCTION METHOD FOR MODIFIED CONJUGATED DIENE-BASED COPOLYMER USING SAME, AND RUBBER COMPOSITION COMPRISING MODIFIED CONJUGATED DIENE-BASED COPOLYMER PRODUCED IN ACCORDANCE THEREWITH

(71) Applicant: LG Chem, Ltd., Seoul (KR)

(72) Inventors: Sang-Mi Lee, Daejeon (KR); Ro-Mi Lee, Daejeon (KR); No-Ma Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/117,080

(22) PCT Filed: Nov. 20, 2015

(86) PCT No.: PCT/KR2015/012560
§ 371 (c)(1),
(2) Date: Aug. 5, 2016

(87) PCT Pub. No.: WO2016/089035
PCT Pub. Date: Jun. 9, 2016

(65) Prior Publication Data
US 2016/0347877 A1 Dec. 1, 2016

(30) Foreign Application Priority Data

Dec. 1, 2014 (KR) .................. 10-2014-0169533
Aug. 11, 2015 (KR) .................. 10-2015-0113476

(51) Int. Cl.
| | | |
|---|---|---|
| C08F 8/42 | (2006.01) | |
| C08F 30/08 | (2006.01) | |
| C08K 3/00 | (2006.01) | |
| B60C 1/00 | (2006.01) | |
| C08F 36/06 | (2006.01) | |
| C08C 19/22 | (2006.01) | |
| C08C 19/25 | (2006.01) | |
| C08C 19/44 | (2006.01) | |
| C08F 236/10 | (2006.01) | |
| C08K 3/36 | (2006.01) | |
| C07D 207/06 | (2006.01) | |
| B01J 23/04 | (2006.01) | |

(52) U.S. Cl.
CPC .............. *C08F 8/42* (2013.01); *B60C 1/0016* (2013.01); *C07D 207/06* (2013.01); *C08C 19/22* (2013.01); *C08C 19/25* (2013.01); *C08C 19/44* (2013.01); *C08F 30/08* (2013.01); *C08F 36/06* (2013.01); *C08F 236/10* (2013.01); *C08K 3/00* (2013.01); *C08K 3/36* (2013.01); *B01J 23/04* (2013.01)

(58) Field of Classification Search
CPC .. C08F 8/42; C08F 30/08; C08F 36/06; B60C 1/0016; C07D 207/06; B01J 23/04
See application file for complete search history.

(56) References Cited

U.S. PATENT DOCUMENTS

| | | |
|---|---|---|
| 6,825,306 B2 | 11/2004 | Halasa et al. |
| 2004/0116635 A1 | 6/2004 | Halasa et al. |
| 2006/0247360 A1 | 11/2006 | Halasa et al. |
| 2010/0099795 A1 | 4/2010 | Uesaka |
| 2010/0152364 A1 | 6/2010 | Wong et al. |
| 2011/0124771 A1 | 5/2011 | Sandstrom et al. |

(Continued)

FOREIGN PATENT DOCUMENTS

| | | |
|---|---|---|
| EP | 1854839 A1 | 11/2007 |
| EP | 2003146 A2 | 12/2008 |

(Continued)

OTHER PUBLICATIONS

Extended Search Report from European Application No. 15865743.7, dated Oct. 28, 2016.

(Continued)

*Primary Examiner* — Margaret Moore
(74) *Attorney, Agent, or Firm* — Lerner, David, Littenberg, Krumholz & Mentlik, LLP

(57) ABSTRACT

Disclosed are an anionic polymerization initiator, which is an organo-alkali metal compound having an anionic end including an amine group, a method of preparing a modified conjugated diene-based polymer using the same, and a rubber composition including the modified conjugated diene-based polymer prepared thereby. Specifically the polydiene and the anionic initiator contain a group of Chemical Formula 8, below,

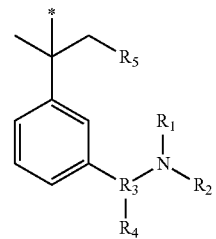

in Chemical Formula 8, $R_1$ and $R_2$ are each independently a C1-C20 alkyl group, $R_3$ is a C1-C10 alkylene group, $R_4$ and $R_5$ each independently a C1-C10 alkyl group, $R_1$ and $R_2$ are linked with each other to form a ring structure, and * represents a bonding position.

10 Claims, No Drawings

(56) References Cited

U.S. PATENT DOCUMENTS

2012/0259056 A1    10/2012   Suzuki et al.
2014/0200306 A1     7/2014   Cho et al.
2014/0243476 A1     8/2014   Lee et al.

FOREIGN PATENT DOCUMENTS

| EP | 2196326 A1 | 6/2010 |
|---|---|---|
| EP | 2325027 A1 | 5/2011 |
| JP | S62149708 A | 7/1987 |
| JP | H09278828 A | 10/1997 |
| JP | 2006257260 A | 9/2006 |
| JP | 2010116546 A | 5/2010 |
| JP | 5568860 B2 | 8/2014 |
| KR | 20070117626 A | 12/2007 |
| KR | 20110056238 A | 5/2011 |
| KR | 20120064698 A | 6/2012 |
| KR | 20130090811 A | 8/2013 |

OTHER PUBLICATIONS

Halasa, et al., "The Chemical Modification of Polymers." The Science and Technology of Rubber, Dec. 31, 2016, XP002762921, vol. 11, pp. 517-520.
International Search Report from PCT/KR2015/012560, dated Mar. 10, 2016.

ANIONIC POLYMERIZATION INITIATOR HAVING ANIONIC TERMINAL COMPRISING AMINE GROUP, PRODUCTION METHOD FOR MODIFIED CONJUGATED DIENE-BASED COPOLYMER USING SAME, AND RUBBER COMPOSITION COMPRISING MODIFIED CONJUGATED DIENE-BASED COPOLYMER PRODUCED IN ACCORDANCE THEREWITH

CROSS-REFERENCE TO RELATED APPLICATION

This application is a national phase entry under 35 U.S.C. §371 of International Application No. PCT/KR2015/012560, filed Nov. 20, 2015, which claims priority to Korean Patent Application No. 10-2014-0169533, filed Dec. 1, 2014 and Korean Patent Application No. 10-2015-0113476, filed Aug. 11, 2015, the disclosures of which are incorporated herein by reference.

TECHNICAL FIELD

The present invention relates to an anionic polymerization initiator having an anionic end including an amine group, a method of preparing a modified conjugated diene-based copolymer using the same, and a rubber composition including a modified conjugated diene-based copolymer prepared thereby.

BACKGROUND ART

Recently, in the vehicle industry, the demand for vehicles to exhibit increased durability, stability and fuel economy is ongoing, and much effort is directed to satisfying the demand.

In particular, many attempts have been made to enhance the properties of rubber, as a material for vehicle tires, especially tire treads, which are in contact with roads. The rubber composition for a vehicle tire contains a conjugated diene-based polymer, such as polybutadiene or butadiene-styrene polymer.

Thorough research is currently ongoing into the addition of various reinforcing agents to conjugated diene-based rubber compositions to increase the performance of vehicle tires. Specifically, as vehicles are required to exhibit stability, durability and fuel economy, rubber compositions having good processability and high mechanical strength, including wear resistance, are being developed as material for vehicle tires, especially tire treads, which are in contact with roads.

DISCLOSURE

Technical Problem

An object of the present invention is to provide an anionic polymerization initiator having an anionic end including an amine group.

Another object of the present invention is to provide a method of preparing a modified conjugated diene-based polymer using the anionic polymerization initiator, and a modified conjugated diene-based polymer prepared thereby.

Still another object of the present invention is to provide a rubber composition that includes the modified conjugated diene-based polymer and exhibits improved heat build-up and high tensile strength, wear resistance and wet skid resistance.

Yet another object of the present invention is to provide a tire including the rubber composition.

Technical Solution

In order to accomplish the above objects, the present invention provides a modified conjugated diene-based polymer represented by any one of Chemical Formulas 1 to 3 below:

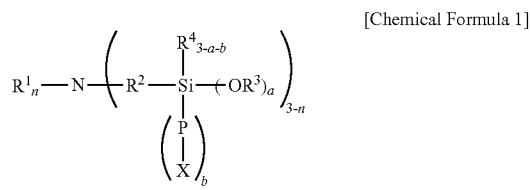

[Chemical Formula 1]

in Chemical Formula 1, $R^1$ is a C1-C10 alkyl or alkylsilyl group, $R^2$ is a C1-C10 alkylene or alkylsilylene group, $R^3$ and $R^4$ are each a C1-C10 alkyl group, P is a conjugated diene-based polymer chain, X is a substituent represented by Chemical Formula 8 below, a is 0, 1, or 2, b is 1, 2, or 3, a+b is 1, 2, or 3, n is an integer of 0 to 2, and two $R^1$s, which are linked with nitrogen, are identical to or different from each other when n is 2, and $R^2$, $R^3$ and $R^4$ are identical to or different from each other when 3-n is 2 or more;

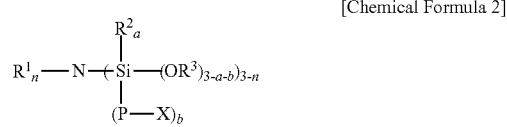

[Chemical Formula 2]

in Chemical Formula 2, $R^1$ is a C1-C10 alkyl or alkylsilyl group, $R^2$ and $R^3$ are each a C1-C10 alkyl group, P is a conjugated diene-based polymer chain, X is a substituent represented by Chemical Formula 8 below, a is an integer of 1 or 2, b is 1, 2, or 3, a+b is 1 or 2, n is an integer of 0 to 2, and two $R^1$s, which are linked with nitrogen, are identical to or different from each other when n is 2, and $R^2$ and $R^3$ are identical to or different from each other when 3-n is 2 or more;

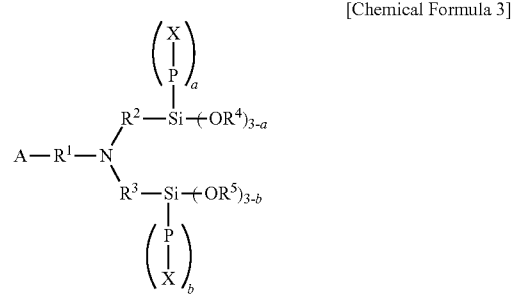

[Chemical Formula 3]

in Chemical Formula 3, A is an amine-containing functional group, P is a conjugated diene-based polymer chain, X is a substituent represented by Chemical Formula 8 below, a and b are each independently 1, 2, or 3, $R^1$, $R^2$ and $R^3$ are each a C1-C10 alkylene or alkylsilylene group, and $R^4$ and $R^5$ are identical to or different from each other and are each a C1-C10 alkyl group; and

[Chemical Formula 8]

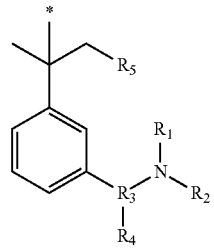

in Chemical Formula 8, $R_1$ and $R_2$ are each independently a C1-C20 alkyl group, $R_3$ is a C1-C10 alkylene group, $R_4$ and $R_5$ are each independently a C1-C10 alkyl group, $R_1$ and $R_2$ are linked with each other to form a ring structure, and * represents a bonding position.

In addition, the present invention provides a method of preparing a modified conjugated diene-based polymer, comprising: a) polymerizing a conjugated diene monomer or a conjugated diene monomer and an aromatic vinyl monomer using a hydrocarbon solvent in the presence of a compound represented by Chemical Formula 4 below, thus forming an active polymer having an alkali metal end, and b) modifying the active polymer having the alkali metal end with a compound represented by Chemical Formula 5, 6 or 7 below:

[Chemical Formula 4]

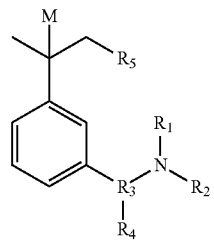

in Chemical Formula 4, $R_1$ and $R_2$ are each independently a C1-C20 alkyl group, $R_3$ is a C1-C10 alkylene group, $R_4$ and $R_5$ are each independently a C1-C10 alkyl group, M is an alkali metal, and $R_1$ and $R_2$ are linked with each other to form a ring structure;

[Chemical Formula 5]

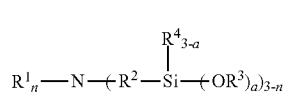

in Chemical Formula 5, $R^1$ is a C1-C10 alkyl or alkylsilyl group, $R^2$ is a C1-C10 alkylene or alkylsilylene group, $R^3$ and $R^4$ are each a C1-C10 alkyl group, a is an integer of 1 to 3, n is an integer of 0 to 2, and two $R^1$s, which are linked with nitrogen, are identical to or different from each other when n is 2, and $R^2$, $R^3$ and $R^4$ are identical to or different from each other when 3-n is 2 or more;

[Chemical Formula 6]

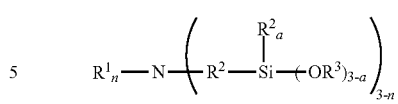

in Chemical Formula 6, $R^1$ is a C1-C10 alkyl or alkylsilyl group, $R^2$ and $R^3$ are each a C1-C10 alkyl group, a is an integer of 1 or 2, n is an integer of 0 to 2, and two $R^1$s, which are linked with nitrogen, are identical to or different from each other when n is 2, and $R^2$ and $R^3$ are identical to or different from each other when 3-n is 2 or more; and

[Chemical Formula 7]

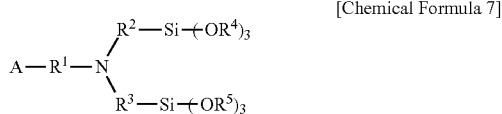

in Chemical Formula 7, A is an amine-containing functional group, $R^1$, $R^2$ and $R^3$ are each a C1-C10 alkylene or alkylsilylene group, and $R^4$ and $R^5$ are identical to or different from each other and are each a C1-C10 alkyl group.

In addition, the present invention provides an anionic polymerization initiator, which is a compound represented by Chemical Formula 4 below:

[Chemical Formula 4]

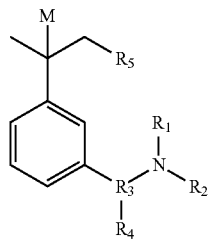

in Chemical Formula 4, $R_1$ and $R_2$ are each independently a C1-C20 alkyl group, $R_3$ is a C1-C10 alkylene group, $R_4$ and $R_5$ are each independently a C1-C10 alkyl group, M is an alkali metal, and $R_1$ and $R_2$ are linked with each other to form a ring structure.

In addition, the present invention provides a modified conjugated diene-based polymer rubber composition including the modified conjugated diene-based polymer prepared by the above method, and a tire including the rubber composition.

Advantageous Effects

According to the present invention, a modified conjugated diene-based polymer, which has high compatibility with an inorganic filler and improved processability, can be provided, and a rubber composition including the modified conjugated diene-based polymer can be employed in manufacturing tires that exhibit improved heat build-up and high tensile strength, wear resistance and wet skid resistance, as well as low rolling resistance.

BEST MODE

Hereinafter, a detailed description will be given of the present invention.

The present invention addresses a modified conjugated diene-based polymer represented by any one of Chemical Formulas 1 to 3 below:

[Chemical Formula 1]

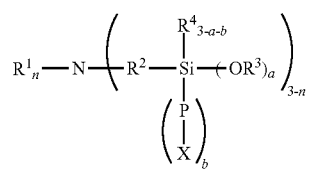

in Chemical Formula 1, $R^1$ is a C1-C10 alkyl or alkylsilyl group, $R^2$ is a C1-C10 alkylene or alkylsilylene group, $R^3$ and $R^4$ are each a C1-C10 alkyl group, P is a conjugated diene-based polymer chain, X is a substituent represented by Chemical Formula 8 below, a is 0, 1, or 2, b is 1, 2, or 3, a+b is 1, 2, or 3, n is an integer of 0 to 2, and two $R^1$s, which are linked with nitrogen, are identical to or different from each other when n is 2, and $R^2$, $R^3$ and $R^4$ are identical to or different from each other when 3-n is 2 or more;

[Chemical Formula 2]

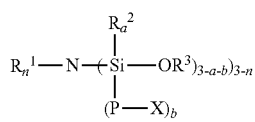

in Chemical Formula 2, $R^1$ is a C1-C10 alkyl or alkylsilyl group, $R^2$ and $R^3$ are each a C1-C10 alkyl group, P is a conjugated diene-based polymer chain, X is a substituent represented by Chemical Formula 8 below, a is an integer of 1 or 2, b is 1, 2, or 3, a+b is 1 or 2, n is an integer of 0 to 2, and two $R^1$s, which are linked with nitrogen, are identical to or different from each other when n is 2, and $R^2$ and $R^3$ are identical to or different from each other when 3-n is 2 or more;

[Chemical Formula 3]

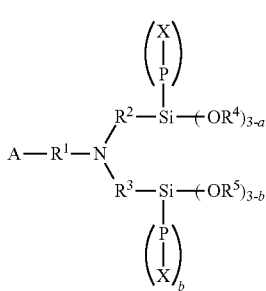

in Chemical Formula 3, A is an amine-containing functional group, P is a conjugated diene-based polymer chain, X is a substituent represented by Chemical Formula 8 below, a and b are each independently 1, 2, or 3, $R^1$, $R^2$ and $R^3$ are each a C1-C10 alkylene or alkylsilylene group, and $R^4$ and $R^5$ are identical to or different from each other and are each a C1-C10 alkyl group; and

[Chemical Formula 8]

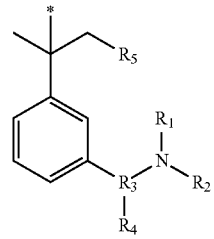

in Chemical Formula 8, $R_1$ and $R_2$ are each independently a C1-C20 alkyl group, $R_3$ is a C1-C10 alkylene group, $R_4$ and $R_5$ are each independently a C1-C10 alkyl group, $R_1$ and $R_2$ are linked with each other to form a ring structure, and * represents a bonding position.

In addition, the present invention addresses a method of preparing a modified conjugated diene-based polymer, comprising: a) polymerizing a conjugated diene monomer or a conjugated diene monomer and an aromatic vinyl monomer using a hydrocarbon solvent in the presence of a compound represented by Chemical Formula 4 below, thus forming an active polymer having an alkali metal end, and b) coupling or reacting the active polymer having the alkali metal end with a compound represented by Chemical Formula 5, 6 or 7 below:

[Chemical Formula 4]

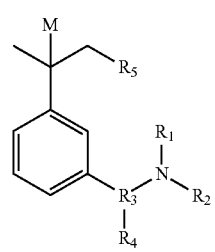

in Chemical Formula 4, $R_1$ and $R_2$ are each independently a C1-C20 alkyl group, $R_3$ is a C1-C10 alkylene group, $R_4$ and $R_5$ are each independently a C1-C10 alkyl group, M is an alkali metal, and $R_1$ and $R_2$ are linked with each other to form a ring structure;

[Chemical Formula 5]

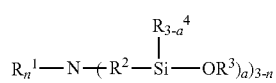

in Chemical Formula 5, $R^1$ is a C1-C10 alkyl or alkylsilyl group, $R^2$ is a C1-C10 alkylene or alkylsilylene group, $R^3$ and $R^4$ are each a C1-C10 alkyl group, a is an integer of 1 to 3, n is an integer of 0 to 2, and two $R^1$s, which are linked with nitrogen, are identical to or different from each other when n is 2, and $R^2$, $R^3$ and $R^4$ are identical to or different from each other when 3-n is 2 or more;

[Chemical Formula 6]

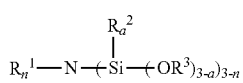

in Chemical Formula 6, $R^1$ is a C1-C10 alkyl or alkylsilyl group, $R^2$ and $R^3$ are each a C1-C10 alkyl group, a is an integer of 1 or 2, n is an integer of 0 to 2, and two $R^1$s, which are linked with nitrogen, are identical to or different from each other when n is 2, and $R^2$ and $R^3$ are identical to or different from each other when 3-n is 2 or more; and

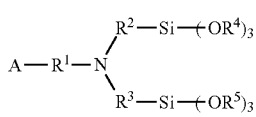

[Chemical Formula 7]

in Chemical Formula 7, A is an amine-containing functional group, $R^1$, $R^2$ and $R^3$ are each a C1-C10 alkylene or alkylsilylene group, and $R^4$ and $R^5$ are identical to or different from each other and are each a C1-C10 alkyl group.

The hydrocarbon solvent is not particularly limited, so long as it is applicable to polymerization of the conjugated diene monomer alone or to copolymerization thereof, and may include at least one selected from the group consisting of n-pentane, n-hexane, n-heptane, isooctane, cyclohexane, toluene, benzene, and xylene.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The aromatic vinyl monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Particularly useful is styrene or α-methylstyrene.

In an embodiment of the present invention, the compound represented by Chemical Formula 4 may be used in an amount of 0.01 to 10 mmol, 0.05 to 5 mmol, 0.1 to 2 mmol, or 0.1 to 1 mmol, based on 100 g in total of the monomer. When the amount of the compound represented by Chemical Formula 4 falls in the above range, a conjugated diene-based polymer optimal for preparing a modified conjugated diene-based polymer may be obtained.

The molar ratio of the compound represented by Chemical Formula 4 and the compound represented by Chemical Formula 5, 6 or 7 may be, for example, 1:0.1 to 1:10, and preferably 1:0.3 to 1:2. When this molar ratio falls in the above range, a modification reaction may be conducted so as to impart optimal performance to the conjugated diene-based polymer.

As used herein, the active polymer having an alkali metal end refers to a polymer comprising a polymer anion and a metal cation, which are coupled with each other.

In the method of preparing the modified conjugated diene-based polymer according to an embodiment of the present invention, the polymerizing in (a) may be performed with the additional use of a polar additive. The reason why the polar additive is further added is that the reaction rates of the conjugated diene monomer and the aromatic vinyl monomer are controlled by the polar additive.

The polar additive may be a base, or may include ether, amine or mixtures thereof. Specifically, it may be selected from the group consisting of tetrahydrofuran, ditetrahydrofurylpropane, diethylether, cycloamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylenediamine, and is preferably ditetrahydropropylpropane, triethylamine, or tetramethylethylenediamine.

The polar additive may be used in an amount of 0.001 to 50 g, 0.001 to 10 g, 0.005 to 1 g, or 0.005 to 0.1 g, based on 100 g in total of the added monomer.

The polar additive may be used in an amount of 0.001 to 10 g, 0.005 to 1 g, or 0.005 to 0.1 g, based on 1 mmol in total of the added compound represented by Chemical Formula 4.

When the conjugated diene monomer and the aromatic vinyl monomer are copolymerized, a block copolymer may be easily prepared due to the difference in the reaction rates therebetween. However, when the polar additive is added, the low reaction rate of the aromatic vinyl compound may be increased to thus obtain the microstructure of the corresponding copolymer, for example, a random copolymer.

In a), the polymerization may be exemplified by anionic polymerization, and particularly, may be living anionic polymerization, in which an active end is obtained through a growth reaction involving anions.

Also, the polymerization in a) may be either high-temperature polymerization or room-temperature polymerization.

High-temperature polymerization is a polymerization process that comprises adding the organometallic compound and then applying heat to increase the reaction temperature, and room-temperature polymerization is a polymerization process that takes place in such a way that heat is not applied after the organometallic compound is added.

The polymerization in a) may take place at a temperature ranging from −20 to 200° C., 0 to 150° C., or 10 to 120° C.

Also, b) may be performed at 0 to 90° C. for 1 min to 5 hr.

The method of preparing the modified conjugated diene-based polymer according to an embodiment of the present invention may be carried out in a batch manner, or alternatively in a continuous manner using at least one reactor.

The modified conjugated diene-based polymer may have a number average molecular weight (Mn) of 1,000 to 2,000,000 g/mol, preferably 10,000 to 1,000,000 g/mol, and more preferably 100,000 to 1,000,000 g/mol. When the number average molecular weight thereof falls in the above range, a modification reaction may be efficiently carried out, or desired properties may be obtained.

The modified conjugated diene-based polymer may have a polydispersity index (Mw/Mn) of 1 to 10, preferably 1 to 5, and more preferably 1 to 4. When the polydispersity index of the modified conjugated diene-based polymer falls in the above range, mixing with inorganic particles may be efficiently carried out, thus ensuring desired properties and remarkably increasing processability.

The modified conjugated diene-based polymer has a vinyl content of 10 wt % or more, preferably 15 wt % or more, and more preferably 20 to 70 wt %.

The vinyl content refers to the amount of a monomer having a vinyl group, or the amount of 1,2-added conjugated diene monomer rather than the amount of 1,4-added conjugated diene monomer, based on 100 wt % of the conjugated diene monomer.

When the vinyl content of the modified conjugated diene-based polymer falls in the above range, the glass transition temperature of the polymer may be elevated. Thus, when such a polymer is applied to tires, the properties required of tires, such as running resistance and wet grip, may be satisfied, and superior fuel economy may result.

The modified conjugated diene-based polymer may have a conjugated diene-based polymer chain comprising the aromatic vinyl monomer in an amount of 0.0001 to 50 wt %, 10 to 40 wt %, or 20 to 40 wt %, based on 100 wt % in total of the conjugated diene monomer and the aromatic vinyl monomer.

The modified conjugated diene-based polymer may have a Mooney viscosity of 40 or more, preferably from 40 to 100, and more preferably from 45 to 90. When the Mooney viscosity thereof falls in the above range, an end-modified conjugated diene-based polymer having improved heat build-up and high processability, compatibility, tensile strength, wear resistance, fuel economy and wet skid resistance may be prepared.

In addition, the present invention addresses an anionic polymerization initiator, which is a compound represented by Chemical Formula 4 below:

[Chemical Formula 4]

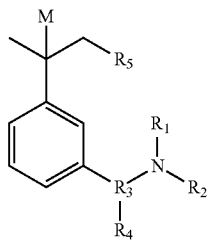

in Chemical Formula 4, $R_1$ and $R_2$ are each independently a C1-C20 alkyl group, $R_3$ is a C1-C10 alkylene group, $R_4$ and $R_5$ are each independently a C1-C10 alkyl group, M is an alkali metal, and $R_1$ and $R_2$ are linked with each other to form a ring structure.

The compound represented by Chemical Formula 4 is an organo-alkali metal compound having an anionic end including an amine group.

The amine group may be cyclic amine, for example, a pyrrolidino group or a piperidino group.

In Chemical Formula 4, M is an alkali metal, preferably lithium.

The compound represented by Chemical Formula 4 may be obtained by reacting methylstyrene including an amine group with an organo-alkali metal compound.

The organo-alkali metal compound may include at least one selected from the group consisting of methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium, 4-butylphenyllithium, 4-tolyllithium, cyclohexyllithium, 3,5-di-n-heptylcyclohexyllithium, and 4-cyclopentyllithium. Preferably useful as the organometallic compound is n-butyllithium, sec-butyllithium, or a mixture thereof.

Alternatively, the organometallic compound may include at least one selected from the group consisting of naphthyl sodium, naphthyl potassium, lithium alkoxide, sodium alkoxide, potassium alkoxide, lithium sulfonate, sodium sulfonate, potassium sulfonate, lithium amide, sodium amide, and potassium amide, and may be used in combination with another organometallic compound.

The compound represented by Chemical Formula 4 may be, for example, the compound represented by Chemical Formula 4a below.

[Chemical Formula 4a]

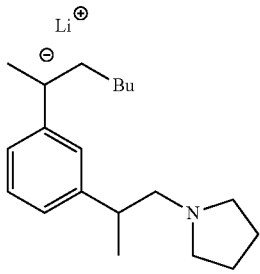

The compound represented by Chemical Formula 4a may be obtained by reacting 3-(2-pyrrolidino-1-methylethyl)-α-methylstyrene with n-butyllithium.

In addition, the present invention addresses a modified conjugated diene-based polymer rubber composition comprising 10 to 100 parts by weight of the modified conjugated diene-based polymer and 0.1 to 200 parts by weight of an inorganic filler, based on 100 parts by weight of the modified conjugated diene-based polymer.

The amount of the inorganic filler may be 10 to 150 parts by weight, or 50 to 100 parts by weight.

The inorganic filler may include at least one selected from the group consisting of silica, carbon black, and a mixture thereof. When the inorganic filler is silica, dispersibility is significantly increased, and the end of the end-modified conjugated diene-based polymer of the invention may couple with silica particles, thus significantly decreasing hysteresis loss.

The modified conjugated diene-based polymer rubber composition may further comprise an additional conjugated diene-based polymer.

Examples of the additional conjugated diene-based polymer may include SBR (styrene-butadiene rubber), BR (butadiene rubber), natural rubber, and mixtures thereof. SBR may be exemplified by SSBR (solution styrene-butadiene rubber).

The modified conjugated diene-based polymer rubber composition may comprise 20 to 100 parts by weight of the modified conjugated diene-based polymer and 0 to 80 parts by weight of the additional conjugated diene-based polymer.

Alternatively, the modified conjugated diene-based polymer rubber composition according to the present invention may comprise 20 to 99 parts by weight of the modified conjugated diene-based polymer and 1 to 80 parts by weight of the additional conjugated diene-based polymer.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent.

Alternatively, the modified conjugated diene-based polymer rubber composition according to the present invention may comprise 10 to 100 parts by weight of the modified conjugated diene-based polymer, 0 to 90 parts by weight of the additional conjugated diene-based polymer, 0 to 100 parts by weight of carbon black, 5 to 200 parts by weight of silica, and 2 to 20 parts by weight of a silane coupling agent, in which the total weight of the modified conjugated diene-based polymer and the additional conjugated diene-based polymer may be 100 parts by weight.

Alternatively, the modified conjugated diene-based polymer rubber composition according to the present invention may comprise 100 parts by weight of a polymer mixture comprising 10 to 99 wt % of the modified conjugated diene-based polymer and 1 to 90 wt % of the additional conjugated diene-based polymer, 1 to 100 parts by weight of carbon black, 5 to 200 parts by weight of silica, and 2 to 20 parts by weight of a silane coupling agent.

Also, the modified conjugated diene-based polymer rubber composition according to the present invention may further comprise 1 to 100 parts by weight of oil. The oil may be exemplified by mineral oil or a softener.

The oil may be used in an amount of 10 to 100 parts by weight, or 20 to 80 parts by weight, based on 100 parts by weight of the conjugated diene-based polymer. Given the above oil content range, desired properties may be exhibited, and the rubber composition may be appropriately softened, thus increasing processability.

In addition, the present invention addresses a tire or tire tread comprising the modified conjugated diene-based polymer rubber composition.

The tire or tire tread is manufactured using the rubber composition including the modified conjugated diene-based polymer, which has high compatibility with an inorganic filler and improved processability, thereby exhibiting superior tensile strength, wear resistance and wet skid resistance and low rolling resistance.

MODE FOR INVENTION

A better understanding of the present invention may be obtained via the following examples. However, the examples of the present invention may be changed in various forms, and are not to be construed as limiting the scope of the present invention. The examples of the present invention are provided to fully describe the present invention to those having ordinary knowledge in the art to which the present invention pertains.

Example 1

8.5 g of 3-(2-pyrrolidino-1-methylethyl)-α-methylstyrene and 18 g of 1.6 M butyllithium were added to 20 g of hexane in a flask and stirred for 1 hr, thus preparing 3-(2-pyrrolidino-1-methylethyl)-α-methylstyrene lithium as a modification initiator.

270 g of styrene, 710 g of 1,3-butadiene, 5000 g of n-hexane, and 1.3 g of 2,2-bis(2-oxolanyl)propane as a polar additive were placed in a 20 L autoclave reactor, and then the temperature inside the reactor was raised to 40° C. When the temperature inside the reactor reached 40° C., 0.4 mmol of 3-(2-pyrrolidino-1-methylethyl)-α-methylstyrene lithium was placed in the reactor, followed by an adiabatic heating reaction. After about 20 min, 20 g of 1,3-butadiene was added. After 5 min, 0.7 g of bis(3-triethoxymethylsilylpropyl)-N-methylamine was added, and the reaction was carried out for 15 min. Then, the polymerization reaction was stopped using ethanol, and 5 mL of a solution of 0.3 wt % BHT (butylated hydroxytoluene) antioxidant in hexane was added.

The resulting polymer was placed in water warmed with steam and stirred to remove the solvent, followed by roll drying to remove the remaining solvent and water, yielding a modified conjugated diene-based polymer. The results of analysis of the modified conjugated diene-based polymer thus obtained are shown in Table 1 below.

Example 2

A modified conjugated diene-based polymer was prepared in the same manner as in Example 1, with the exception that N1,N1,N3,N3-tetramethyl-2-((trimethoxysilyl)methyl)propane-1,3-diamine was used as the modifier, in lieu of bis(3-triethoxymethylsilylpropyl)-N-methylamine.

Example 3

A modified conjugated diene-based polymer was prepared in the same manner as in Example 1, with the exception that 1 g of N,N-bis(triethoxysilylpropyl)aminopropyl-1-imidazole was used as the modifier, in lieu of bis(3-triethoxymethylsilylpropyl)-N-methylamine.

Comparative Example 1

A modified conjugated diene-based polymer was prepared in the same manner as in Example 1, with the exception that butyllithium was used as the initiator.

The conjugated diene-based polymers of Examples 1 to 3 and Comparative Example 1 were analyzed through the following methods.

a) Mooney viscosity: two samples having a weight of 15 g or more were preheated for 1 min and then measured at 100° C. for 4 min using an MV-2000, made by ALPHA Technologies.

b) Styrene monomer (SM) and Vinyl content: measurement was conducted using NMR.

c) Weight average molecular weight (Mw), Number average molecular weight (Mn), and Polydispersity Index (PDI): measurement was conducted via GPC at 40° C. The column used herein was a combination of two PLgel Olexis columns and one PLgel mixed-C column, made by Polymer Laboratories, and all of the replaced columns were mixed bed-type columns. Also, polystyrene (PS) was the GPC standard material for the calculation of molecular weight.

TABLE 1

|  |  | Example | | | C. Ex. |
|---|---|---|---|---|---|
|  |  | 1 | 2 | 3 | 1 |
|  | Sample | A | B | C | A |
| Initiator | Butyllithium | — | — | — | 4 mmol |
|  | a | 4 mmol | 4 mmol | 4 mmol | — |
| Coupling agent (g) | b | 0.7 | — | — | 0.7 |
|  | c | — | 0.7 | — | — |
|  | d | — | — | 1 | — |
| Mooney viscosity (MV) |  | 42 | 44 | 52 | 40 |
| NMR (%) | SM | 27 | 27 | 26 | 27 |
|  | Vinyl | 42 | 42 | 44 | 43 |
| GPC (×10$^4$) | Mp | 25 | 25 | 25 | 25 |
|  | Mn | 39 | 37 | 42 | 39 |
|  | Mw | 57 | 52 | 67 | 54 |
|  | PDI | 1.4 | 1.5 | 1.4 | 1.3 | a: 3-(2-pyrrolidino-1-methylethyl)-α-methylstyrene lithium
b: bis(3-triethoxymethylsilylpropyl)-N-methylamine
c: N1,N1,N3,N3-tetramethyl-2-((trimethoxysilyl)methyl)propane-1,3-diamine
d: N,N-bis(triethoxysilylpropyl)aminopropyl-1-imidazole The conjugated diene-based polymer rubber compositions were prepared using samples A, B, and C shown in Table 1, as raw rubber, under the mixing conditions shown in Table 2 below.

The conjugated diene-based polymer rubber composition was kneaded as follows. Specifically, upon primary kneading, raw rubber (conjugated diene-based polymer), a filler, an organosilane coupling agent, oil, zinc oxide, a stearic acid antioxidant, an anti-aging agent, wax and an accelerator were kneaded at 80 rpm using a Banbury mixer provided with a temperature controller. For this, the temperature of the kneader was controlled, and a first mixture was obtained at a discharge temperature of 140 to 150° C. Upon secondary kneading, the first mixture was cooled to room temperature, after which rubber, sulfur and a vulcanization accelerator were placed in the kneader, and a second mixture was obtained at a discharge temperature of 45 to 60° C. Upon tertiary kneading, the second mixture was molded and vulcanized at 180° C. for T90+10 min using a vulcanization press, thereby manufacturing vulcanized rubber.

TABLE 2

| (unit: parts by weight) | S-1 |
|---|---|
| Rubber | 100.0 |
| Silica | 70.0 |
| Coupling agent | 11.02 |
| Oil | 33.75 |
| Zinc oxide | 3.0 |
| Stearic acid | 2.0 |
| Antioxidant | 2.0 |
| Anti-aging agent | 2.0 |
| Wax | 1.0 |
| Rubber accelerator | 1.75 |
| Sulfur | 1.5 |
| Vulcanization accelerator | 2.0 |
| Total weight | 230.02 |

The properties of the manufactured rubber compositions were measured through the following methods.

1) Tensile Testing

According to the tensile testing method of ASTM 412, the tensile strength upon cutting a test sample and tensile stress (300% modulus) at 300% elongation were measured. For this, a Universal Test Machine 4204, made by Instron, was used, and the tensile strength, modulus, and elongation were measured at a tensile speed of 50 cm/min at room temperature.

2) Viscoelasticity

A dynamic mechanical analyzer made by TA was used. When undergoing strain under conditions of a frequency of 10 Hz in the torsional mode and a measurement temperature (ranging from −60 to 60° C.), the Tan δ of each sample was measured. The Payne effect was represented by the difference between the minimum and the maximum in the strain sweep range of 0.28% to 40%. The lower the Payne effect, the higher the dispersibility of the filler, such as silica. When Tan δ at 0° C., which is a low temperature, was increased, wet skid resistance became superior, and when Tan δ at 60° C., which is a high temperature, was decreased, hysteresis loss was reduced, resulting in low rolling resistance of tires and thus superior fuel economy. Table 3 below shows the properties of the vulcanized rubber.

TABLE 3

|  | Prep. Ex. 1 | Prep. Ex. 2 | Prep. Ex. 3 | C. Prep. Ex. 1 |
|---|---|---|---|---|
| Sample | A | B | C | A |
| 300% Modulus (kgf/cm$^2$) | 129 | 119 | 131 | 109 |
| Tensile strength (kgf/cm$^2$) | 171 | 163 | 191 | 161 |
| Tan δ at 0° C. | 105 | 104 | 101 | 100 |
| Tan δ at 60° C. (Index) | 108 | 106 | 107 | 100 |

As is apparent from the results of Table 3, compared to Comparative Preparation Example 1, the modified conjugated diene-based polymer rubber compositions of Preparation Examples 1 to 3 according to the present invention were significantly increased in 300% modulus (tensile stress) and tensile strength, and exhibited high Tan δ at 60° C. Thus, when the modified conjugated diene-based polymer rubber composition of the invention was used for a tire, rolling resistance was decreased, and thus superior fuel economy resulted.

Furthermore, the modified conjugated diene-based polymer rubber compositions of Preparation Examples 1 and 3 according to the present invention exhibited higher Tan δ at 0° C. than that of Comparative Preparation Example 1. Thus, when the modified conjugated diene-based polymer rubber composition of the invention was used for a tire, high wet skid resistance resulted.

The invention claimed is:

1. A modified conjugated diene-based polymer represented by any one of Chemical Formulas 1 to 3 below:

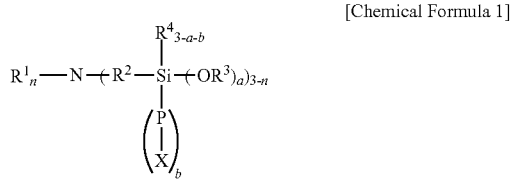

[Chemical Formula 1]

in Chemical Formula 1, $R^1$ is a C1-C10 alkyl or alkylsilyl group, $R^2$ is a C1-C10 alkylene or alkylsilylene group, $R^3$ and $R^4$ are each a C1-C10 alkyl group, P is a conjugated diene-based polymer chain, X is a substituent represented by Chemical Formula 8 below, a is 0, 1, or 2, b is 1, 2, or 3, a+b is 1, 2, or 3, n is an integer of 0 to 2, and two $R^1$s, which are linked with nitrogen, are identical to or different from each other when n is 2, and $R^2$, $R^3$ and $R^4$ are identical to or different from each other when 3-n is 2 or more;

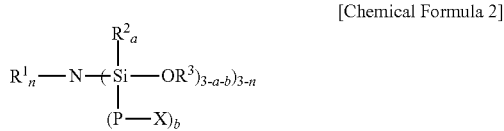

[Chemical Formula 2]

in Chemical Formula 2, $R^1$ is a C1-C10 alkyl or alkylsilyl group, $R^2$ and $R^3$ are each a C1-C10 alkyl group, P is a conjugated diene-based polymer chain, X is a substituent represented by Chemical Formula 8 below, a is an integer of 1 or 2, b is 1, 2, or 3, a+b is 1 or 2, n is an integer of 0 to 2, and two $R^1$s, which are linked with nitrogen, are identical to or different from each other when n is 2, and $R^2$ and $R^3$ are identical to or different from each other when 3-n is 2 or more;

[Chemical Formula 3]

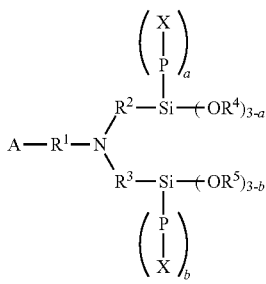

in Chemical Formula 3, A is an amine-containing functional group, P is a conjugated diene-based polymer chain, X is a substituent represented by Chemical Formula 8 below, a and b are each independently 1, 2, or 3, $R^1$, $R^2$ and $R^3$ are each a C1-C10 alkylene or alkylsilylene group, and $R^4$ and $R^5$ are identical to or different from each other and are each a C1-C10 alkyl group; and

[Chemical Formula 8]

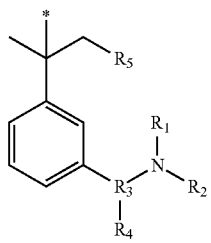

in Chemical Formula 8, $R_1$ and $R_2$ are each independently a C1-C20 alkyl group, $R_3$ is a C1-C10 alkylene group, $R_4$ and $R_5$ are each independently a C1-C10 alkyl group, $R_1$ and $R_2$ are linked with each other to form a ring structure, and * represents a bonding position.

2. A method of preparing a modified conjugated diene-based polymer, comprising:

a) polymerizing a conjugated diene monomer or a conjugated diene monomer and an aromatic vinyl monomer using a hydrocarbon solvent in presence of a compound represented by Chemical Formula 4 below, thus forming an active polymer having an alkali metal end; and b) modifying the active polymer having the alkali metal end with a compound represented by Chemical Formula 5, 6 or 7 below:

[Chemical Formula 4]

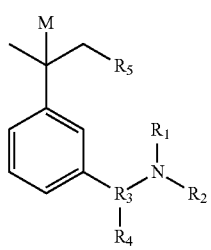

in Chemical Formula 4, $R_1$ and $R_2$ are each independently a C1-C20 alkyl group, $R_3$ is a C1-C10 alkylene group, $R_4$ and $R_5$ are each independently a C1-C10 alkyl group, M is an alkali metal, and $R_1$ and $R_2$ are linked with each other to form a ring structure;

[Chemical Formula 5]

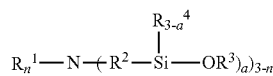

in Chemical Formula 5, $R^1$ is a C1-C10 alkyl or alkylsilyl group, $R^2$ is a C1-C10 alkylene or alkylsilylene group, $R^3$ and $R^4$ are each a C1-C10 alkyl group, a is an integer of 1 to 3, n is an integer of 0 to 2, and two $R^1$s, which are linked with nitrogen, are identical to or different from each other when n is 2, and $R^2$, $R^3$ and $R^4$ are identical to or different from each other when 3-n is 2 or more;

[Chemical Formula 6]

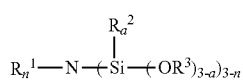

in Chemical Formula 6, $R^1$ is a C1-C10 alkyl or alkylsilyl group, $R^2$ and $R^3$ are each a C1-C10 alkyl group, a is an integer of 1 or 2, n is an integer of 0 to 2, and two $R^1$s, which are linked with nitrogen, are identical to or different from each other when n is 2, and $R^2$ and $R^3$ are identical to or different from each other when 3-n is 2 or more; and

[Chemical Formula 7]

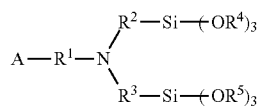

in Chemical Formula 7, A is an amine-containing functional group, $R^1$, $R^2$ and $R^3$ are each a C1-C10 alkylene or alkylsilylene group, and $R^4$ and $R^5$ are identical to or different from each other and are each a C1-C10 alkyl group.

3. The method of claim 2, wherein the compound represented by Chemical Formula 4 is used in an amount of 0.01 to 10 mmol based on 100 g in total of the monomer.

4. The method of claim 2, wherein a molar ratio of the compound represented by Chemical Formula 4 and the compound represented by Chemical Formula 5, 6 or 7 is 1:0.1 to 1:10.

5. The method of claim 2, wherein the polymerizing in a) is performed with additional use of a polar additive.

6. The method of claim 5, wherein the polar additive is added in an amount of 0.001 to 10 g based on 1 mmol in total of the compound represented by Chemical Formula 4.

7. The method of claim 2, wherein the modified conjugated diene-based polymer has a number average molecular weight (Mn) of 1,000 to 2,000,000 g/mol.

8. The method of claim 2, wherein the modified conjugated diene-based polymer includes 0.0001 to 50 wt % of the aromatic vinyl monomer based on 100 wt % in total of the conjugated diene monomer and the aromatic vinyl monomer.

9. An anionic polymerization initiator, which is a compound represented by Chemical Formula 4 below:

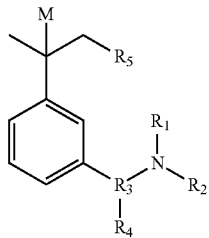

[Chemical Formula 4]

in Chemical Formula 4, $R_1$ and $R_2$ are each independently a C1-C20 alkyl group, $R_3$ is a C1-C10 alkylene group, $R_4$ and $R_5$ are each independently a C1-C10 alkyl group, M is an alkali metal, and $R_1$ and $R_2$ are linked with each other to form a ring structure.

10. The anionic polymerization initiator of claim 9, wherein the compound represented by Chemical Formula 4 is a compound represented by Chemical Formula 4a below

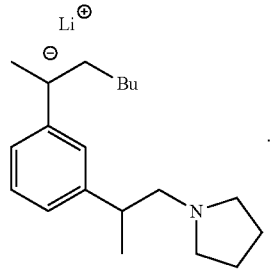

[Chemical Formula 4a]

* * * * *